United States Patent
Kustra et al.

(10) Patent No.: US 11,410,780 B2
(45) Date of Patent: Aug. 9, 2022

(54) APPARATUS AND METHOD FOR PROVIDING FEEDBACK TO A PARTICIPANT OF A COMMUNICATION

(71) Applicant: KONINKLIJKE PHILIPS N.V., Eindhoven (NL)

(72) Inventors: Jacek Lukasz Kustra, Eindhoven (NL); Monique Hendriks, Eindhoven (NL); Pieter Christiaan Vos, Vught (NL); Sergio Consoli, Nuenen (NL); Dimitrios Mavroeidis, Utrecht (NL); Arlette van Wissen, Culemborg (NL); Aart Tijmen van Halteren, Geldrop (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 333 days.

(21) Appl. No.: 16/615,165

(22) PCT Filed: May 16, 2018

(86) PCT No.: PCT/EP2018/062658
§ 371 (c)(1),
(2) Date: Nov. 20, 2019

(87) PCT Pub. No.: WO2018/215253
PCT Pub. Date: Nov. 29, 2018

(65) Prior Publication Data
US 2020/0176130 A1 Jun. 4, 2020

(30) Foreign Application Priority Data
May 24, 2017 (EP) .................................. 17172616

(51) Int. Cl.
*G16H 80/00* (2018.01)
*G06F 3/01* (2006.01)
(Continued)

(52) U.S. Cl.
CPC ............. *G16H 80/00* (2018.01); *G06F 3/015* (2013.01); *G06F 3/017* (2013.01); *G06F 9/542* (2013.01); *H04L 65/40* (2013.01); *H04L 65/80* (2013.01)

(58) Field of Classification Search
CPC ........ G16H 20/17; G16H 50/30; G16H 20/13; G16H 80/00; G06F 3/017; G06F 9/54;
(Continued)

(56) References Cited

U.S. PATENT DOCUMENTS

| 2007/0071206 A1 | 3/2007 | Gainsboro et al. |
| 2009/0204426 A1 | 8/2009 | Thorne et al. |

(Continued)

FOREIGN PATENT DOCUMENTS

WO 2014120291 A1 8/2014

OTHER PUBLICATIONS

International Search and Written Opinion for International Application No. PCT/EP2018/062658, filed May 16, 2018, 15 pages.

*Primary Examiner* — Iqbal Zaidi
(74) *Attorney, Agent, or Firm* — Sherry Austin

(57) ABSTRACT

There is provided an apparatus and a method of operating the apparatus for providing feedback to a participant directing a communication to one or more other participants. The apparatus (100) comprises a processor (102) configured to acquire, from one or more physiological characteristic sensors (104), one or more physiological characteristic signals from at least one participant to which the communication is directed as the communication is received by the at least one participant. The processor (102) is also configured to determine a measure of the quality of the communication based on a comparison of the one or more physiological characteristic signals acquired from the at least one participant with one or more expected physiological characteristic signals
(Continued)

and control a user interface (108) to provide feedback of the determined quality measure of the communication to the participant directing the communication to the at least one participant.

17 Claims, 3 Drawing Sheets

(51) Int. Cl.
*G06F 9/54* (2006.01)
*H04L 65/40* (2022.01)
*H04L 65/80* (2022.01)

(58) Field of Classification Search
CPC ..... A16B 5/14532; A61B 5/1118; A61N 1/05; H04L 29/06; H04L 12/24; H04R 5/027; H04R 5/033; G06T 19/00; G06Q 40/00
See application file for complete search history.

(56) References Cited

U.S. PATENT DOCUMENTS

| | | | |
|---|---|---|---|
| 2010/0304864 A1* | 12/2010 | Johnson | A61B 5/6843 463/36 |
| 2011/0149013 A1 | 6/2011 | Khot et al. | |
| 2011/0201960 A1* | 8/2011 | Price | A61B 5/6804 600/549 |
| 2013/0262132 A1 | 10/2013 | Sant et al. | |
| 2016/0103973 A1 | 4/2016 | Singal et al. | |
| 2017/0076046 A1 | 3/2017 | Barnes et al. | |
| 2021/0350896 A1* | 11/2021 | Shelton, IV | A61M 5/31565 |

* cited by examiner

US 11,410,780 B2

APPARATUS AND METHOD FOR PROVIDING FEEDBACK TO A PARTICIPANT OF A COMMUNICATION

RELATED APPLICATIONS

This application is the U.S. National Phase application under 35 U.S.C. § 371 of International Application No. PCT/EP2018/062658, filed on May 16, 2018, which claims priority to and the benefit of European Application Serial No. 17172616.9, filed May 24, 2017. These applications are hereby incorporated by reference herein, for all purposes.

TECHNICAL FIELD OF THE INVENTION

The invention relates to the field of communications and, in particular, to an apparatus and method for providing feedback to a participant of a communication.

BACKGROUND TO THE INVENTION

There are various situations in which communications between participants can be critical to future events. This is particularly the case in the medical field where communications can impact the health and wellbeing of a patient. For example, meetings between medical personnel (such as tumour board meetings) may make available a large amount of information on individual patients and often result in a decision being taken on the treatment, or follow-up treatment, for the patients.

The decisions taken during these meetings are particularly important as they can have an effect on a patient's life over a long period of time, or even forever. If mistakes are made during the communications in such meetings, wrong decisions may be taken and this can ultimately lead to mistreatment of a patient. The mistreatment of a patient can potentially result in side-effects for the patient. In some cases, the mistreatment of a patient may significantly reduce a life quality of the patient, may lead to serious (and possibly irreversible) health consequences for the patient and, worse still, may reduce a life expectancy of the patient. Also, the side-effects resulting from wrong decisions being taken can have a negative economic impact. For example, a patient may require increased care or regular monitoring as a result of wrong decisions having been taken, which puts an undue burden on medical personnel.

Therefore, a good interaction between medical personnel in such meetings is crucial to ensure that the most appropriate decisions are taken (for example, that the correct treatment is selected) for a patient. However, due to several practical limitations, communications can be compromised and decisions can be negatively impacted as a result. These practical limitations can include, for example, the length of a meeting, the existence of distractions for the participants, boredom of the participants, or similar.

An additional difficulty is that electronic devices are now often used for communication purposes. This is particularly the case with the advances of fast and widespread internet availability as it means that participants are often choosing to communicate remotely. However, the use of electronic devices for communications can make it difficult for a participant initiating a communication to perceive the reaction of other participants receiving the communication. For example, the perception of social signals that can normally be used to gauge the reactions of others during a face-to-face communications is lost when electronic transmission mechanisms are used instead. Also, in some cases, communications no longer occur in real-time such as where communications are initiated in the form of voice messages, text messages, e-mails, or other electronic forms.

US 2013/0262132 is concerned with tracking metrics impacting the behaviour of individuals to provide feedback on the performance of the individual with the aim of optimising performance and productivity in a health care system. The metrics can, for example, be generated using statistical reports related to participation in certain activities such as tumour board meetings. However, the disclosed method focuses on whether individuals that are to participate in certain activities are fit to make decisions and thus the disclosed method still fails to overcome the limitations outlined above, which relate to the risks involved in wrong decisions being taken as a result of compromised communications between participants during collaborative events in which those decisions are taken.

There is thus a need for an improved apparatus and method for providing feedback to a participant of a communication.

SUMMARY OF THE INVENTION

As noted above, the limitation with existing approaches is that wrong decisions may be taken as a result of compromised communications between participants during collaborative events in which those decisions are taken. It would thus be valuable to have an improved apparatus and method for providing feedback to a participant of a communication, which overcomes the existing problems.

Therefore, according to a first aspect of the invention, there is provided an apparatus for providing feedback to a participant directing a communication to one or more other participants. The apparatus comprises a processor configured to acquire, from one or more physiological characteristic sensors, one or more physiological characteristic signals from at least one participant to which the communication is directed as the communication is received by the at least one participant. The processor is also configured to determine a measure of the quality of the communication based on a comparison of the one or more physiological characteristic signals acquired from the at least one participant with one or more expected physiological characteristic signals and control a user interface to provide feedback of the determined quality measure of the communication to the participant directing the communication to the at least one participant.

In some embodiments, the participant directing the communication may be remote from the at least one participant to which the communication is directed.

In some embodiments, the one or more acquired physiological characteristic signals may be indicative of a reaction of the at least one of participant to which the communication is directed. In some embodiments, the one or more expected physiological characteristic signals may be determined based on statistical data, heuristics, or calibration data. In some embodiments, one or more of the expected physiological characteristic signals may be determined based on one or more physiological characteristic signals acquired from the participant directing the communication.

In some embodiments, the determined quality measure of the communication may be a measure of synchrony between at least one characteristic of the one or more physiological characteristic signals acquired from the at least one participant and at least one corresponding characteristic of the one or more expected physiological characteristic signals. In some embodiments, the determined quality measure of the communication may be a measure of a weighted sum of measures of synchrony between characteristics of the one or more physiological characteristic signals acquired from the at least one participant and corresponding characteristics of the one or more expected physiological characteristic signals.

In some embodiments, the processor may be further configured to obtain from a memory or generate, based on the determined quality measure of the communication, an associated recommendation intended to improve the determined quality measure of the communication. In some embodiments, the recommendation may be obtained from the memory or generated when the determined quality measure of the communication is below a minimum threshold.

In some embodiments, the processor may be further configured to control the user interface to provide to the participant directing the communication to the at least one participant a notification indicating the recommendation. In some embodiments, the recommendation may comprise any one or more of: an instruction for the participant directing the communication to repeat the communication, an instruction for the participant directing the communication to review the communication, an instruction for the participant directing the communication to use a different transmission mechanism for the communication, and an instruction for the participant directing the communication to classify the determined quality measure of the communication for storage.

In some embodiments, the one or more physiological characteristic sensors may comprise one or more sensors configured to acquire signals indicative of any one or more of: a motion of the at least one participant to which the communication is directed, a heart rate of the at least one participant to which the communication is directed, a respiration rate of the at least one participant to which the communication is directed, a posture of the at least one participant to which the communication is directed, a pose of the at least one participant to which the communication is directed, a voice tone of the at least one participant to which the communication is directed, one or more gestures initiated by the at least one participant to which the communication is directed, a change in a facial skin colour of the at least one participant to which the communication is directed, and a skin response of the at least one participant to which the communication is directed.

In some embodiments, the apparatus may further comprise one or more of one or more of the physiological characteristic sensors configured to acquire one or more physiological characteristic signals from the at least one participant to which the communication is directed and the user interface configured to provide the feedback on the determined quality measure of the communication.

According to a second aspect of the invention, there is provided a method of operating an apparatus comprising a processor to provide feedback to a participant directing a communication to one or more other participants. The method comprises acquiring, by the processor from one or more physiological characteristic sensors, one or more physiological characteristic signals from at least one participant to which the communication is directed as the communication is received by the at least one participant and determining, by the processor, a measure of the quality of the communication based on a comparison of the one or more physiological characteristic signals acquired from the at least one participant with one or more expected physiological characteristic signals. The method also comprises controlling, by the processor, a user interface to provide feedback of the determined quality measure of the communication to the participant directing the communication to the at least one participant.

According to a third aspect of the invention, there is provided a computer program product comprising a computer readable medium, the computer readable medium having computer readable code embodied therein, the computer readable code being configured such that, on execution by a suitable computer or processor, the computer or processor is caused to perform the method or the methods described above.

According to the aspects and embodiments described above, the limitations of existing techniques are addressed. In particular, according to the above-described aspects and embodiments, it is possible to obtain a measurement of communication quality (or perform a quality assessment) during a communication, which can be used to provide feedback to the participant directing or initiating the communication. More specifically, it is possible to assess participants of a communication in relation to other participants of the communication to measure, feedback and improve on the quality of the communication. The participant directing or initiating the communication is provided with valuable information that can be used to appropriately alter the manner in which the communication is provided in order to obtain high quality communications. The high quality communications that are achieved can improve the decisions that are taken during collaborative events. This is particularly valuable where the communications are linked to critical decisions, such as communications between medical personnel that are linked to medical decisions for patients. The feedback provided according to the above-described aspects and embodiments can be used to optimise those decisions.

There is thus provided an improved apparatus and method for providing feedback to a participant of a communication, which overcomes the existing problems.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As noted above, the invention provides an improved apparatus and method for providing feedback to a participant of a communication, overcoming existing problems.

In any of the embodiments described herein, one or more of the participant directing the communication and at least one participant to which the communication is directed may, for example, be a medical personnel (such as a doctor, a nurse, or any other medical personnel). However, it will be understood that the apparatus 100 and method described herein is in fact suitable for a communication between any type of participants, or between any combinations of types of participants. In some embodiments, the participant directing the communication may be remote from the at least one participant to which the communication is directed. For example, the participants may be at different locations or in different environments (such as in different rooms or buildings). Alternatively, the participant directing the communication may be local to the at least one participant to which the communication is directed. For example, the participants may be at the same location or in the same environment (such as in the same room or building). The participant directing the communication may also be referred to as the sender, the initiator, the emitter, or the transmitter of the communication. The participant to which the communication is directed may also be referred to as the receiver of the communication.

In any of the embodiments described herein, the transmission mechanism for the communication may be an electronic transmission mechanism. For example, a participant may operate an electronic device to initiate (or send or transmit) the communication. The communication itself can thus be an electronic communication or a communication provided via an electronic communication channel. An electronic communication channel may be an encrypted electronic communication channel or an unencrypted electronic communication channel. Examples of a communication include, but are not limited to, an electronic message (such as a voice message, a text message, a video message, an e-mail, or any other message received electronically), a call (such as a voice call, a video call, or any other type of call), a communication via an application or service running on an electronic device, or any other type of communication.

Figure 1:
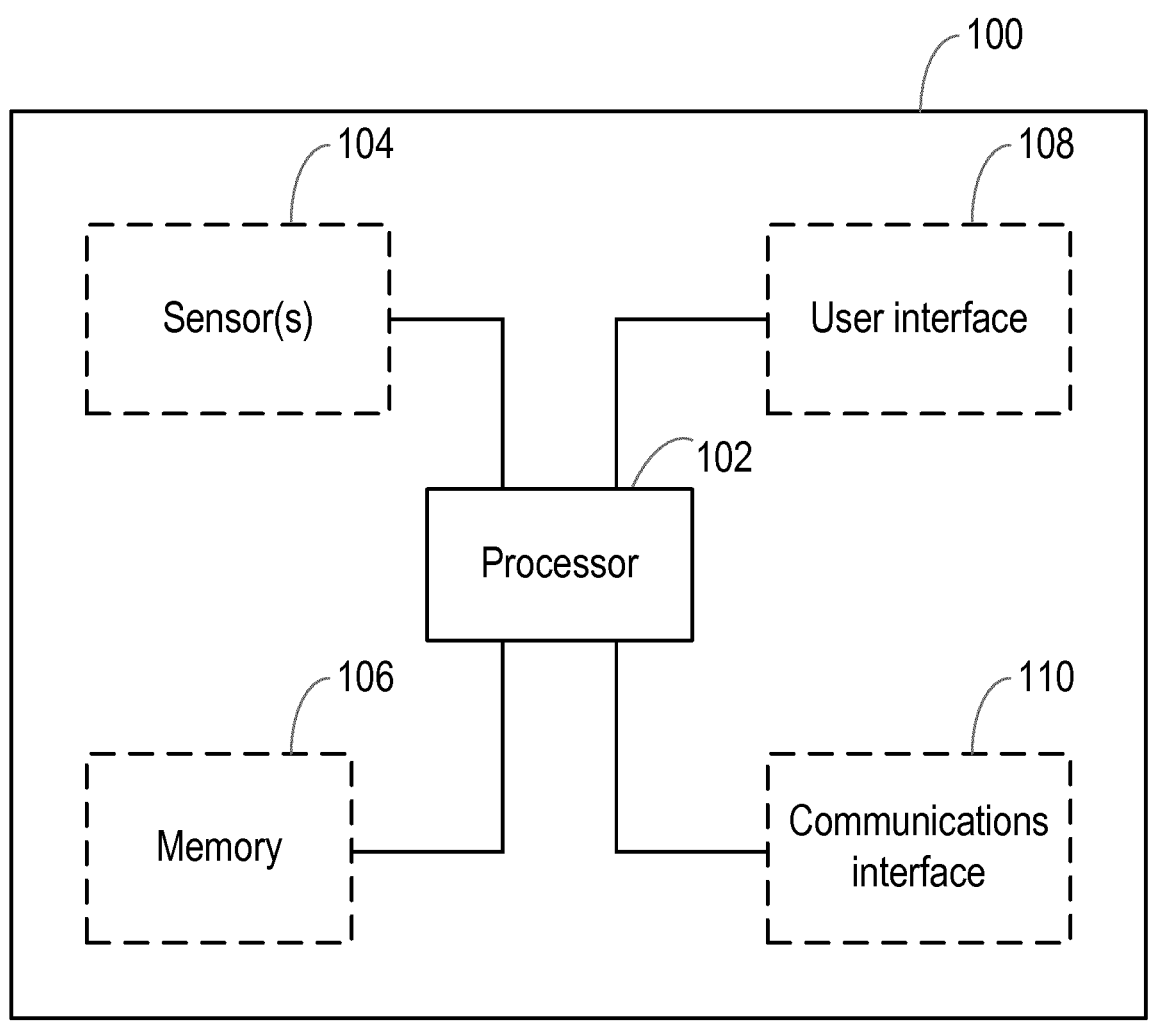
FIG. 1 is a block diagram of an apparatus according to an embodiment.

FIG. 1 illustrates an example of an apparatus 100 for providing feedback to a participant directing a communication to one or more other participants according to an embodiment. With reference to FIG. 1, the apparatus 100 comprises a processor 102 that controls the operation of the apparatus 100 and that can implement the method described herein. The processor 102 can comprise one or more processors, processing units, multi-core processors or modules that are configured or programmed to control the apparatus 100 in the manner described herein. In particular implementations, the processor 102 can comprise a plurality of software and/or hardware modules that are each configured to perform, or are for performing, individual or multiple steps of the method according to embodiments of the invention.

Briefly, the processor 102 is configured to acquire, from one or more physiological characteristic sensors 104, one or more physiological characteristic signals from at least one participant to which the communication is directed as the communication is received by the at least one participant and to determine a measure of the quality of the communication based on a comparison of the one or more physiological characteristic signals acquired from the at least one participant with one or more expected physiological characteristic signals.

The one or more physiological characteristic signals that are acquired by the processor 102 can be any physiological characteristic signals that are indicative of a reaction of the at least one of participant to the communication. The one or more physiological characteristic signals may, for example, be any physiological characteristic signals that can provide an indication of a quality of the communication. In some embodiments, the physiological characteristic signals may be non-verbal signals, which can be used in a social context to provide an indication of communication quality. A participant of a communication may create non-verbal signals both consciously and unconsciously. The one or more physiological characteristic signals that are acquired by the processor 102 from one or more physiological characteristic sensors 104 may be indicative of measures of one or more social characteristics such as empathy, rapport, interpersonal connectedness, agreement, or similar, between the participants of the communication, and can provide an indication of the overall attention devoted by the participant directing the communication to the at least one participant.

Examples of the one or more physiological characteristic sensors 104 include, but are not limited to, one or more sensors that are configured to acquire signals indicative of any one or more of a motion (such as a head motion, or any other motion) of the at least one participant to which the communication is directed (for example, a motion sensor such as an accelerometer, a camera, or any other motion sensor, or any combination of motion sensors), a heart rate of the at least one participant to which the communication is directed (for example, a heart rate sensor such as an electrocardiogram (ECG) sensor, a photoplethysmogram (PPG) sensor, or any other heart rate sensor, or any combination of heart rate sensors), a respiration rate of the at least one participant to which the communication is directed (for example, a respiration rate sensor such as an acoustic sensor, an airflow sensor, a motion sensor such as those configured for the chest and abdomen, an electrocardiogram (ECG) sensor, a radar sensor, an optical sensor, a thermal sensor, or any other respiration rate sensor, or any combination of respiration rate sensors), a posture of the at least one participant to which the communication is directed (for example, a posture sensor such as a camera, or any other posture sensor, or any combination of posture sensors), a pose of the at least one participant to which the communication is directed (for example, a pose sensor such as a camera, or any other pose sensor, or any combination of pose sensors), a voice tone of the at least one participant to which the communication is directed (for example, an audio sensor such as a microphone, or any other audio sensor, or any combination of audio sensors), one or more gestures initiated by the at least one participant to which the communication is directed (for example, a visual sensor such as a camera, or any other visual sensor, or any combination of visual sensors), a change in a facial skin colour (such as blushing) of the at least one participant to which the communication is directed (for example, a skin colour sensor such as a photometric light reflection sensor, or any other skin colour sensor, or any combination of skin colour sensors), a skin response (such as a perspiration or sweat rate) of the at least one participant to which the communication is directed (for example, a skin response sensor such as a galvanic skin response (GSR) sensor, or any other skin response sensor), or any other sensor, or any combination of sensors, suitable to acquire physiological characteristic signals from at least one participant to which the communication is directed.

A pose of the at least one participant to which the communication is directed can be a position assumed by the at least one participant to which the communication is directed, such as sitting, standing, laying, or any other position that may be assumed by the at least one participant to which the communication is directed. A posture of the at least one participant to which the communication is directed can be a manner in which the at least one participant to which the communication is directed holds their body (e.g. when in a particular pose), such as slouching when sitting or standing.

As illustrated in FIG. 1, according to some embodiments, the apparatus 100 itself can comprise one or more physiological characteristic sensors 104 configured to acquire one or more physiological characteristic signals from the at least one participant to which the communication is directed. Alternatively or in addition, one or more physiological characteristic sensors 104 configured to acquire one or more physiological characteristic signals from the at least one participant to which the communication is directed may be external to (i.e. separate to or remote from) the apparatus 100. For example, at least one physiological characteristic sensor 104 may be part of, or embedded in, another device. In some embodiments, a wearable device (such as a smart watch) configured to be worn by the participant to which a communication is directed and/or any other type of device (e.g. a smart device such as a tablet device, smart phone, or similar) may comprise at least one of the one or more physiological characteristic sensors 104. Alternatively or in addition, at least one of the one or more physiological characteristic sensors 104 may be provided in a predetermined location at which (or an environment in which) the participant to which a communication is directed is to receive the communication. In some embodiments, the apparatus 100 itself may be a wearable device (for example, a smart watch, a monitoring device, or any other wearable device), a portable electronic device (for example, a smart device such as a tablet device, a smart phone, or any other portable electronic device), or any other device.

As mentioned earlier, a measure of the quality of the communication is determined by the processor 102 of the apparatus 100 based on a comparison of the one or more physiological characteristic signals acquired from the at least one participant with one or more expected physiological characteristic signals. The one or more expected physiological characteristic signals can, for example, be determined based on statistical data, heuristics, or calibration data. In some embodiments, at least one of the one or more expected physiological characteristic signals may be stored in one or more memories 106. As illustrated in FIG. 1, according to some embodiments, the apparatus 100 itself can comprise one or more memories 104. Alternatively, one or more memories 104 may be external to (i.e. separate to or remote from) the apparatus 100. For example, one or more memories 104 may be part of another device. In any of the embodiments described herein, one or more of the expected physiological characteristic signals may be determined based on one or more physiological characteristic signals acquired from the participant directing the communication.

In addition to being configured to acquire one or more physiological characteristic signals and to determine a quality measure of the communication, the processor 102 of the apparatus 100 is also configured to control a user interface 108 to provide (for example, render, output, or display) feedback of the determined quality measure of the communication to the participant directing the communication to the at least one participant. As illustrated in FIG. 1, according to some embodiments, the apparatus 100 itself can comprise a user interface 108 that is configured to provide the feedback on the determined quality measure of the communication. Alternatively or in addition, a user interface 108 that is configured to provide the feedback on the determined quality measure of the communication may be external to (i.e. separate to or remote from) the apparatus 100. For example, the user interface 108 may be part of another device. In some embodiments, a wearable device (such as a smart watch) configured to be worn by the participant directing the communication and/or any other type of device (e.g. a smart device such as a tablet device, smart phone, or similar) may comprise at least one of the user interface 108. In some embodiments, the apparatus 100 may comprise both the user interface 108 and one or more physiological characteristic sensors, or the user interface 108 and one or more physiological characteristic sensors may be part of the same external device. In addition to or as an alternative to being configured to provide the feedback on the determined quality measure of the communication, a user interface 108 may be configured to receive a user input. In other words, a user interface 108 may allow a user to manually enter data, instructions, or information. In these embodiments, the processor 102 can be configured to acquire the user input from one or more user interfaces 108.

Thus, a user interface 108 may be any user interface that enables feedback of the determined quality measure of the communication to be provided (for example, rendered, output, or displayed) to the participant directing the communication to the at least one participant and, alternatively or in addition, a user interface 108 may be any user interface that enables a user of the apparatus 100 to provide a user input, interact with and/or control the apparatus 100. For example, a user interface 108 may comprise one or more switches, one or more buttons, a keypad, a keyboard, a mouse, a touch screen or an application (for example, on a smart device such as a tablet, a smartphone, or any other smart device), a display or display screen, a graphical user interface (GUI) or any other visual component, one or more speakers, one or more microphones or any other audio component, one or more lights (such as light emitting diode LED lights), a component for providing tactile or haptic feedback (such as a vibration function, or any other tactile feedback component), an augmented reality device (such as augmented reality glasses, or any other augmented reality device), a smart device (such as a tablet, a smart phone, a smart watch, or any other smart device), or any other user interface, or combination of user interfaces. In some embodiments, the user interface 108 that is controlled to provide (for example, render, output, or display) may be the same user interface 108 as that which enables the user to provide a user input, interact with and/or control the apparatus 100.

In some embodiments, the processor 102 of the apparatus 100 can be further configured to obtain from a memory 106 or generate, based on the determined quality measure of the communication, an associated recommendation intended to improve the determined quality measure of the communication. In some embodiments, the recommendation may be obtained from the memory 106 or generated when the determined quality measure of the communication is below a minimum threshold. In some embodiments, the processor 102 can be further configured to control the user interface 108 to provide to the participant directing the communication to the at least one participant a notification indicating the recommendation.

As illustrated in FIG. 1, in some embodiments, the apparatus 100 may also comprise a communications interface (or circuitry) 110 for enabling the apparatus 100 to communicate with (or connect to) any components, interfaces, units, memories, sensors and devices that are internal or external to the apparatus 100. For example, the communications interface 110 may be configured to communicate with the one or more physiological characteristic sensors 104, one or more memories 106, and/or the user interface 108. In any of the embodiments described herein, the communications interface 110 may be configured to communicate with any components, interfaces, units, memories, sensors and devices wirelessly or via a wired connection.

It will be appreciated that FIG. 1 only shows the components required to illustrate this aspect of the invention and, in a practical implementation, the apparatus 100 may comprise additional components to those shown. For example, the apparatus 100 may comprise a battery or other power supply for powering the apparatus 100 or means for connecting the apparatus 100 to a mains power supply.

Figure 2:
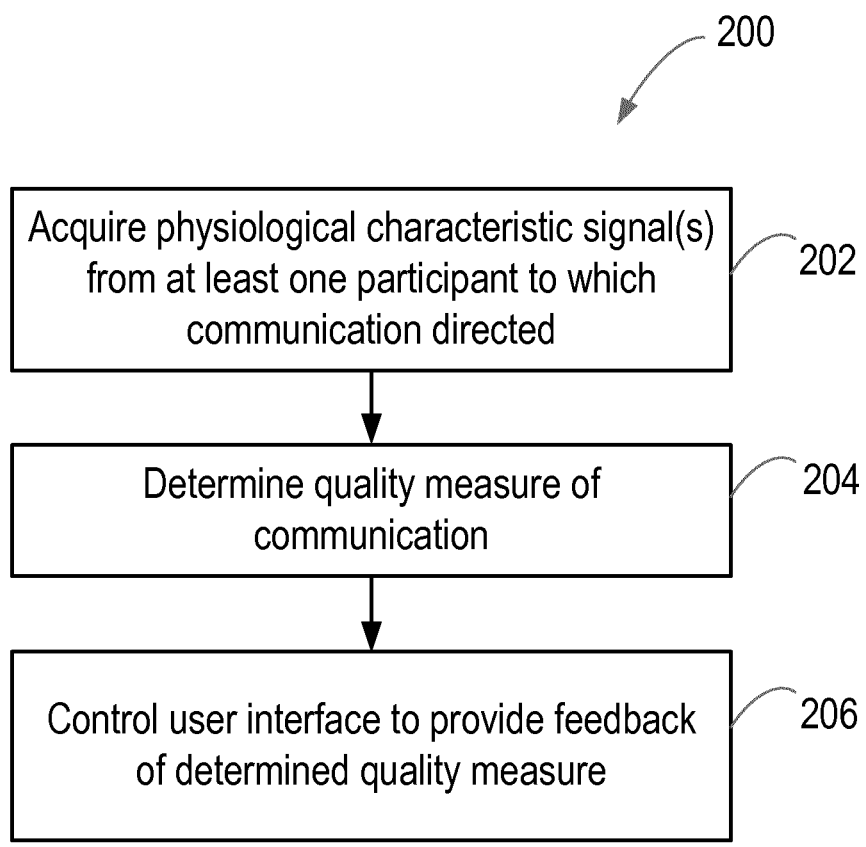
FIG. 2 is a flow chart illustrating a method according to an embodiment.

FIG. 2 illustrates a method 200 of operating an apparatus 100 comprising a processor 102 to provide feedback to a participant directing a communication to one or more other participants according to an embodiment. The illustrated method 200 of FIG. 2 can generally be performed by or under the control of the processor 102 of the apparatus 100.

With reference to FIG. 2, at block 202, one or more physiological characteristic signals are acquired by the processor 102 from at least one participant to which the communication is directed as the communication is received by the at least one participant (or while the at least one participant is receiving the communication). In other words, the processor 102 gathers physiological characteristic data on the at least one participant to which the communication is directed (or the receiver of the communication). The physiological characteristic signals may be acquired non-invasively by the one or more physiological characteristic sensors 104, meaning that the acquisition of physiological characteristic signals does not actively interfere with the participant from which the signals are acquired during with the communication. The processor 102 is configured to acquire the one or more physiological characteristic signals from one or more physiological characteristic sensors 104. As mentioned earlier, the one or more physiological characteristic signals acquired by the processor 102 from one or more physiological characteristic sensors 104 can be any physiological characteristic signals that are indicative of a reaction of the at least one of participant to which the communication is directed.

Once the processor 102 has acquired the one or more physiological characteristic signals, the processor 102 then processes the one or more acquired physiological characteristic signals. More specifically, at block 204 of FIG. 2, a measure of the quality of the communication is determined by the processor 102 based on a comparison of the one or more physiological characteristic signals acquired from the at least one participant with one or more expected physiological characteristic signals. Thus, the one or more acquired physiological characteristic signals are used to asses the communication quality. In some embodiments, the one or more acquired physiological characteristic signals may be processed to derive measures of one or more social characteristics (such as the empathy, rapport, interpersonal connectedness, agreement, attention devoted, or similar, between the participants of the communication), which can be used to assess the communication quality.

As mentioned earlier, the one or more expected physiological characteristic signals to which the one or more physiological characteristic signals are compared can, for example, be determined based on statistical data, heuristics, or calibration data. The calibration data may, for example, comprise data that is specific to the at least one participant from which the one or more physiological characteristic signals are acquired. In some embodiments, at least one of the one or more expected physiological characteristic signals may be stored in one or more memories 106. As mentioned earlier, in any of the embodiments described herein, one or more of the expected physiological characteristic signals may be determined based on one or more physiological characteristic signals acquired from the participant directing the communication to the at least one participant.

In some embodiments, the quality measure of the communication that is determined by the processor 100 based on the comparison can, for example, be a measure of synchrony between at least one characteristic (or at least one feature) of the one or more physiological characteristic signals acquired from the at least one participant and at least one corresponding characteristic of the one or more expected physiological characteristic signals. A characteristic (or feature) of a physiological characteristic signal can be any characteristic that is suitable for providing an indication of a quality measure of the communication. An example of such a characteristic of a heart rate signal is a heart rate variability, an example of such a characteristic of a voice signal is a voice tone, and so on.

In some embodiments, the synchrony can be determined between at least one feature $F_{1A} \ldots F_{nA}$ of the one or more physiological characteristic signals acquired from the at least one participant and the same at least one feature $F_{1B} \ldots F_{nB}$ of the one or more expected physiological characteristic signals. A measure of the synchrony between features can be representative of a similarity between specific features (for example, a mimicking of movement or tone of voice, or similar) or a similarity between a flow of features (for example, fluent transitions such as in turn taking, regulatory gestures like head nods, or similar). For two corresponding features $F_{iA}$ and $F_{iB}$, the measure of synchrony $S_i$ can be expressed as:

$$S_i = F_{iA} \sim F_{iB}.$$

In some embodiments, the synchrony between a plurality of features may be measured. For example, the one or more physiological characteristic signals may comprise a voice signal, which can have a plurality of characteristics (or features), such as pitch, intonation, intensity, and so on. In some embodiments, the measure of synchrony may be determined for all features. The synchrony can be measured using any technique suitable for measuring synchrony of which a person skilled in the art will be aware. Examples of techniques for measuring synchrony include, but are not limited to, using a time lagged cross-correlation between time series of physiological characteristic signals, and using recurrence analysis. However, a skilled person will be aware of other techniques that are also suitable for determining a measure of synchrony. A measure of synchrony can be representative of the communication quality (for example, the quality of relations) between the participant directing the communication and one or more of the at least one participants to which the communication is directed.

The higher the synchrony between at least one characteristic of the one or more physiological characteristic signals acquired from the at least one participant and at least one corresponding characteristic of the one or more expected physiological characteristic signals, the higher the quality measure. Similarly, the lower the synchrony between the at least one characteristic of the one or more physiological characteristic signals acquired from the at least one participant and the at least one corresponding characteristic of the one or more expected physiological characteristic signals, the lower the quality measure. For example, participants of a communication that are determined to have a synchronised heart rate variability are more likely to achieve a higher quality communication than those that have an asynchronous heart rate variability. Similarly, for example, participants of a communication that are determined to have synchronous head motion are more likely to achieve a higher quality communication than those that have an asynchronous head motion. Also, for example, participants of a communication that perform synchronous agreeable reactions (such as, nodding head motions, thumbs up actions, verbal approvals, or any other agreeable reactions, or any combination of agreeable reactions) are more likely to achieve a higher quality communication than those that do not perform synchronous agreeable reactions or those that perform conflicting reactions.

In some embodiments, the quality measure of the communication that is determined by the processor 100 based on the comparison of the one or more physiological characteristic signals acquired from the at least one participant and the corresponding characteristics (or features) of the one or more expected physiological characteristic signals can, for example, be a measure of a weighted sum of measures of synchrony between characteristics of the one or more physiological characteristic signals acquired from the at least one participant and the corresponding characteristics of the one or more expected physiological characteristic signals. For example, the measure of synchrony determined for all individual features may be combined to result in a measure for a quality of the relationship Q between the participant directing the communication and one or more of the at least one participants to which the communication is directed.

In embodiments where the measure of synchrony represents the quality of the relationship Q between a participant A directing the communication and a participant B to which the communication is directed, the quality of the relationship Q may, for example, be determined as follows:

$$Q_{AB} = \sum_{i=1}^{n} \omega_i S_i,$$

where ω to is the weight indicative of the extent to which each synchrony measure S of a specific feature contributes to the overall quality of the relationship Q between the participants A and B. For example, the feature of the tone of voice may be considered more important for the relationship quality Q than the heart rate variability. The importance of features in relation to one another can thus be expressed through the associated weight ω.

Although examples have been provide for the determination of a quality measure of the communication (such as the measure of synchrony or the weighted sum of measures of synchrony), it will be understood that any other quality measure may be determined.

Returning back to FIG. 2, at block 206, a user interface 106 is controlled by the processor 102 to provide feedback of the determined quality measure of the communication to the participant directing the communication to the at least one participant. In this way, feedback on the communication quality as generated by the processor 102 can be provided, which can help improve the communication.

Although not illustrated in FIG. 2, in some embodiments, the method 200 may further comprise obtaining from a memory 106 or generating, by the processor 102, an associated recommendation (or intervention) that is intended to improve the determined quality measure of the communication (for example, to improve a level of synchrony). The recommendation is obtained from a memory 106 or generated based on the determined quality measure of the communication. For example, a memory 106 may store quality measures of communications with associated recommendations that are intended to improve the quality measure. In some embodiments, the recommendation may be obtained from a memory 106 or generated when the determined quality measure of the communication is below a minimum threshold.

For example, in embodiments where a quality of the relationship Q between the participant directing the communication and one or more of the at least one participants to which the communication is directed is determined, it may be determined whether this value Q is above or below a threshold value τ. If the value Q is below the threshold value τ, the processor 102 may be configured to obtain from a memory 106 or generate recommendations on how to improve the quality of the relationship Q. These recommendations can depend on certain characteristics of the measured features, expressed by a weight v. In some embodiments, the weight v can be representative of the ease by which the participant directing the communication is able to change a characteristic (or feature) to produce a change in the quality of the relationship Q. For example, the characteristic of a tone of voice is easier to change than the characteristic of a heart rate variability.

Thus, according to some embodiments, a recommendation R for a participant A directing the communication may be expressed as follows:

$$R_A = \mathrm{argmax}_i(v_i S_i).$$

This function results in the highest contributing weighted feature $F_i$. This feature may then be used to obtain a recommendation from a memory 106. In a memory 106, there may be recommendations stored with one or more features. For example, a feature 'posture' may be stored with the recommendation such as 'Try to mimic the posture of your partner', while a feature 'turn-taking' may be stored with the recommendation such as 'Try to make sure that interruptions are kept to a minimum. Let your partner finish before starting to speak'.

In any of the embodiments described herein where a recommendation is obtained or generated by the processor 102, the method can also further comprise controlling, by the processor 102, the user interface 108 to provide a notification indicating the recommendation to the participant directing the communication to the at least one participant. In this way, it is possible to aid the participant directing the communication to the at least one participant in improving the communication.

Examples for the recommendation include, but are not limited to any one or more of an instruction for the participant directing the communication to repeat the communication, an instruction for the participant directing the communication to review the communication (e.g. an instruction for the participant directing the communication to assess the communication to determine whether a change is needed to improve the quality measure of the communication), an instruction for the participant directing the communication to use a different transmission mechanism for the communication, an instruction for the participant directing the communication to classify the determined quality measure of the communication for storage (for example, for archive purposes), or any other recommendation, or combination of recommendations, that is aimed at improving the determined quality measure of the communication.

In some embodiments, the quality measure of the communication that is determined by the processor 100 may be used together with a risk level associated with a decision that is linked to the communication to obtain from a memory 106 or generate a recommendation. In these embodiments, a quality threshold may be set for the quality measure of the communication, where a communication having a quality measure above the quality threshold is classed as having a high communication quality and a communication having a quality measure below the quality threshold is classed as having a low communication quality. Similarly, a risk threshold may be set for the risk level associated with a decision that is linked to the communication, where a risk level above the risk threshold is classed as a high risk decision (which may have potentially detrimental consequences) and a risk level below the risk threshold is classed as a low risk decision. The quality threshold and the risk threshold may be used to classify the quality measure and the risk level respectively to determine when a recommendation is to be triggered by the processor 102.

An example of the quality threshold and risk threshold in use is provided below:

|  | Low Risk Decision | High Risk Decision |
| --- | --- | --- |
| High Communication Quality | Proceed with decision | Proceed with decision |
| Low Communication Quality | Flag Decision - Accept | Flag Decision - Double check |

Thus, in this example, where the quality measure of a communication is determined to be high, irrespective of whether the risk level associated with a decision linked to the communication is determined to be low or high, the decision is allowed to proceed without a recommendation being triggered by the processor 102. Where the quality measure of a communication is determined to be low and the risk level associated with a decision linked to the communication is determined to be low, the decision is flagged but accepted by the processor 102. Where the quality measure of a communication is determined to be low and the risk level associated with a decision linked to the communication is determined to be high, the decision is flagged and a recommendation is triggered by the processor 102. In this example, the recommendation indicates that the decision (or the assessment leading to the decision) needs to be double checked (or repeated) to ensure a high communication quality.

Figure 3:
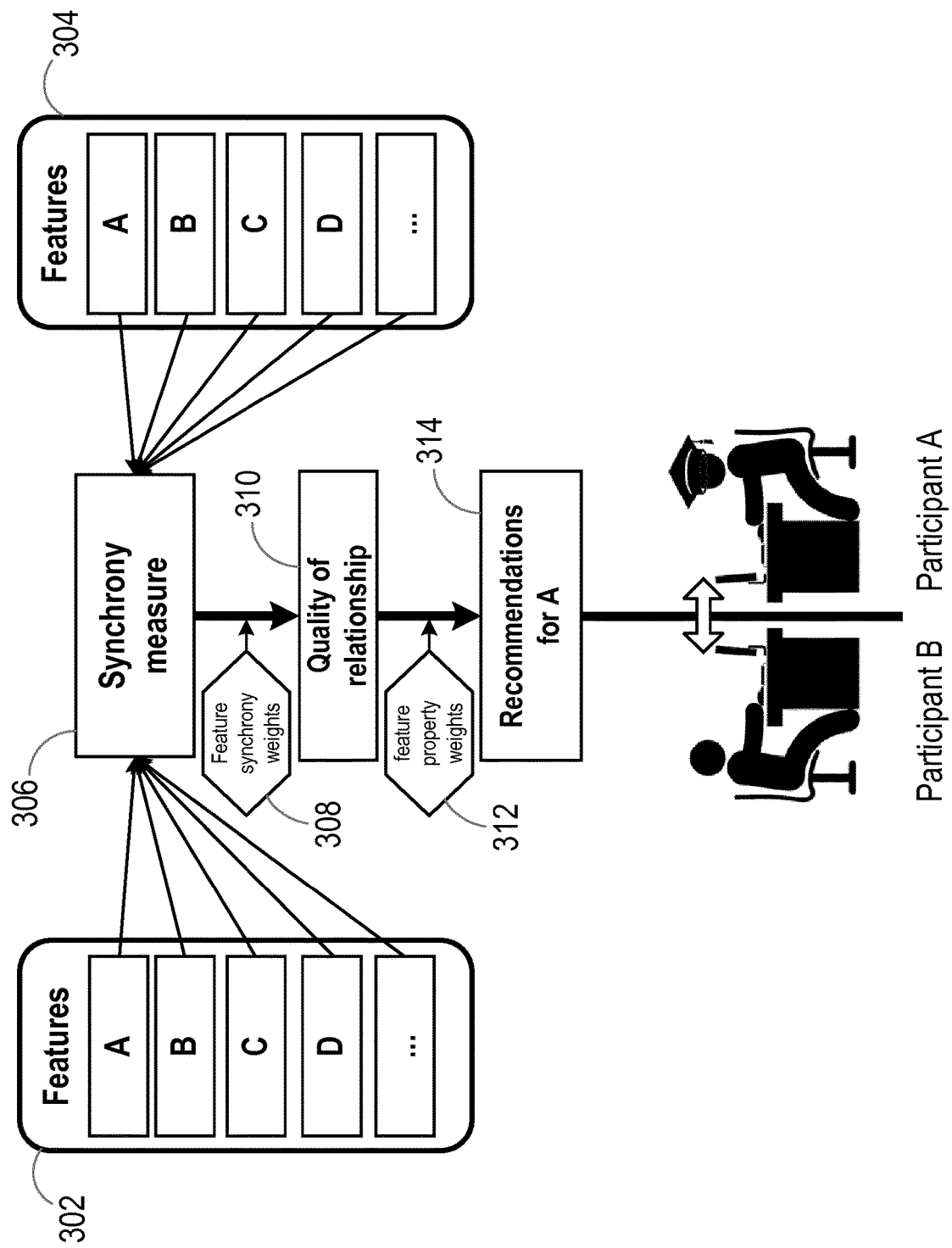
FIG. 3 is a flow chart illustrating a method according to an example embodiment.

FIG. 3 illustrates a method of operating an apparatus 100 comprising a processor 102 to provide feedback to a participant directing a communication to one or more other participants according to an example embodiment. The illustrated method of FIG. 3 can generally be performed by or under the control of the processor 102 of the apparatus 100. In this example embodiment, a participant A and a participant B are in communication with each other.

With reference to FIG. 3, at block 302, a physiological characteristic signal is acquired by the processor 102 from participant A to which a communication is directed from participant B, where the physiological characteristic signal is acquired as the communication is received by the participant A. Similarly, at block 304 of FIG. 3, a physiological characteristic signal is acquired by the processor 102 from participant B to which a communication is directed from participant A, where the physiological characteristic signal is acquired as the communication is received by the participant B. The physiological characteristic signals acquired at blocks 302 and 304 each comprise a plurality of characteristics (or features) A, B, C, D.

At blocks 306, 308, 310 and 312 of FIG. 3, for each participant A and B, a measure of the quality of the communication directed to the other participant is determined by the processor 102 based on a comparison of the physiological characteristic signal acquired from the participant to which the communication is directed with one or more expected physiological characteristic signals. More specifically, in this example embodiment, the quality measure of the communication that is determined by the processor 100 based on the comparison comprises a measure of synchrony between at least one characteristic A, B, C, D of the physiological characteristic signal acquired from the participant to which the communication is directed and at least one corresponding characteristic A, B, C, D of the one or more expected physiological characteristic signals. According to some embodiments, one or more of the expected physiological characteristic signals may be determined based on the physiological characteristic signal acquired from the participant directing the communication. The measure of synchrony is determined at block 306 for each of the features A, B, C, D. Then, at block 308, the features are weighted according to their importance (for example, the extent to which the synchrony measure of a specific feature contributes to the overall quality).

At block 310 of FIG. 3, the measure of synchrony determined for all individual features is combined to obtain a measure for a quality of the relationship Q between the participants A and B of the communication. Then, at block 312, the features are weighted according to the ease by which the participant directing the communication to the other participant is able to change a feature to produce a respective change in the quality of the relationship Q. At block 314, a recommendation intended to improve the determined quality measure of the communication (for example, to improve the level of synchrony) is obtained from a memory 106 or is generated by the processor 102 and a user interface 108 is controlled by the processor 102 to provide a notification indicating the recommendation to the participant directing the communication to the other participant.

In any of the embodiments described herein, the method for providing feedback to a participant directing a communication described herein may be performed in respect of a single participant to which the communication is directed as the communication is received by that participant or in respect of a plurality of participants to which the communication is directed as the communication is received by those participants. For example, in some embodiments, the method described herein may be performed simultaneously in respect of a plurality of participants to which the communication is directed as the communication is received by those participants.

There is therefore provided an improved apparatus and method for providing feedback to a participant of a communication. The apparatus and method described herein can be useful in any communication setting where the quality of communication is important and thus the assessment of the communication quality will be beneficial. For example, the apparatus and method described herein can be particularly useful for medical communications (e.g. medical meetings such as tumour board meetings).

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention.

It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for providing feedback to a participant directing a communication to one or more other participants, the apparatus comprising:
a processor configured to:
acquire, from one or more physiological characteristic sensors, one or more physiological characteristic signals from at least one participant to which the communication is directed as the communication is received by the at least one participant;
determine a measure of the quality of the communication based on a comparison of the one or more physiological characteristic signals acquired from the at least one participant with one or more expected physiological characteristic signals, wherein the determined quality measure of the communication is a measure of a weighted sum of measures of synchrony between characteristics of the one or more physiological characteristic signals acquired from the at least one participant and corresponding characteristics of the one or more expected physiological characteristic signals; and
control a user interface to provide feedback of the determined quality measure of the communication to the participant directing the communication to the at least one participant.

2. An apparatus as claimed claim 1, wherein the participant directing the communication is remote from the at least one participant to which the communication is directed.

3. An apparatus as claimed in claim 1, wherein the one or more acquired physiological characteristic signals are indicative of a reaction of the at least one of participant to which the communication is directed.

4. An apparatus as claimed in claim 1, wherein the one or more expected physiological characteristic signals are determined based on statistical data, heuristics, or calibration data.

5. An apparatus as claimed in claim 1, wherein one or more of the expected physiological characteristic signals are determined based on one or more physiological characteristic signals acquired from the participant directing the communication.

6. An apparatus as claimed in claim 1, wherein the processor is further configured to:
obtain from a memory or generate, based on the determined quality measure of the communication, an associated recommendation intended to improve the determined quality measure of the communication.

7. An apparatus as claimed in claim 6, wherein the recommendation is obtained from the memory or generated when the determined quality measure of the communication is below a minimum threshold.

8. An apparatus as claimed in claim 6, wherein the processor is further configured to:
control the user interface to provide to the participant directing the communication to the at least one participant a notification indicating the recommendation.

9. An apparatus as claimed in claim 6, wherein the recommendation comprises any one or more of:
an instruction for the participant directing the communication to repeat the communication;
an instruction for the participant directing the communication to review the communication;
an instruction for the participant directing the communication to use a different transmission mechanism for the communication; and
an instruction for the participant directing the communication to classify the determined quality measure of the communication for storage.

10. An apparatus as claimed in claim 1, wherein the one or more physiological characteristic sensors comprise one or more sensors configured to acquire signals indicative of any one or more of:
- a motion of the at least one participant to which the communication is directed;
- a heart rate of the at least one participant to which the communication is directed;
- a respiration rate of the at least one participant to which the communication is directed;
- a posture of the at least one participant to which the communication is directed;
- a pose of the at least one participant to which the communication is directed;
- a voice tone of the at least one participant to which the communication is directed;
- one or more gestures initiated by the at least one participant to which the communication is directed;
- a change in a facial skin colour of the at least one participant to which the communication is directed; and
- a skin response of the at least one participant to which the communication is directed.

11. An apparatus as claimed in claim 1, wherein the apparatus further comprises one or more of:
- one or more of the physiological characteristic sensors configured to acquire one or more physiological characteristic signals from the at least one participant to which the communication is directed; and
- the user interface configured to provide the feedback on the determined quality measure of the communication.

12. A method of operating an apparatus comprising a processor to provide feedback to a participant directing a communication to one or more other participants, the method comprising:
- acquiring, by the processor from one or more physiological characteristic sensors, one or more physiological characteristic signals from at least one participant to which the communication is directed as the communication is received by the at least one participant;
- determining, by the processor, a measure of the quality of the communication based on a comparison of the one or more physiological characteristic signals acquired from the at least one participant with one or more expected physiological characteristic signals, wherein the determined quality measure of the communication is a measure of a weighted sum of measures of synchrony between characteristics of the one or more physiological characteristic signals acquired from the at least one participant and corresponding characteristics of the one or more expected physiological characteristic signals; and
- controlling, by the processor, a user interface to provide feedback of the determined quality measure of the communication to the participant directing the communication to the at least one participant.

13. A computer program product comprising a non-transitory computer readable medium, the non-transitory computer readable medium comprising computer readable code being configured such that, on execution by a suitable computer or processor, the computer or processor is caused to perform the method as claimed in claim 12.

14. A method of operating an apparatus comprising a processor to provide feedback to a participant directing a communication to one or more other participants, the method comprising:
- acquiring, by the processor from one or more physiological characteristic sensors, one or more physiological characteristic signals from at least one participant to which the communication is directed as the communication is received by the at least one participant;
- determining, by the processor, a measure of the quality of the communication based on a comparison of the one or more physiological characteristic signals acquired from the at least one participant with one or more expected physiological characteristic signals;
- obtaining, by the processor, based on the determined quality measure of the communication, an associated recommendation intended to improve the determined quality measure of the communication, wherein the recommendation is obtained from memory or generated when the determined quality measure of the communication is below a minimum threshold; and
- controlling, by the processor, a user interface to provide feedback of the determined quality measure of the communication to the participant directing the communication to the at least one participant.

15. The method of claim 14, wherein the determined quality measure of the communication is a measure of synchrony between at least one characteristic of the one or more physiological characteristic signals acquired from the at least one participant and at least one corresponding characteristic of the one or more expected physiological characteristic signals.

16. The method of claim 14, wherein the determined quality measure of the communication is a measure of a weighted sum of measures of synchrony between characteristics of the one or more physiological characteristic signals acquired from the at least one participant and corresponding characteristics of the one or more expected physiological characteristic signals.

17. A method of operating an apparatus comprising a processor to provide feedback to a participant directing a communication to one or more other participants, the method comprising:
- acquiring, by the processor from one or more physiological characteristic sensors, one or more physiological characteristic signals from at least one participant to which the communication is directed as the communication is received by the at least one participant;
- determining, by the processor, a measure of the quality of the communication based on a comparison of the one or more physiological characteristic signals acquired from the at least one participant with one or more expected physiological characteristic signals; and
- obtaining, by the processor, based on the determined quality measure of the communication, an associated recommendation intended to improve the determined quality measure of the communication;
- controlling, by the processor, a user interface to provide feedback of the determined quality measure of the communication and a notification indicating the recommendation to the participant directing the communication to the at least one participant.

* * * * *